US010034668B2

(12) United States Patent
Ebner

(10) Patent No.: US 10,034,668 B2
(45) Date of Patent: Jul. 31, 2018

(54) CIRCULAR KNIFE BLADE FOR LINEAR STAPLERS

(71) Applicant: Covidien LP, Mansfield, MA (US)

(72) Inventor: Timothy D. Ebner, New Haven, CT (US)

(73) Assignee: Covidien LP, Mansfield, MA (US)

( * ) Notice: Subject to any disclaimer, the term of this patent is extended or adjusted under 35 U.S.C. 154(b) by 595 days.

(21) Appl. No.: 14/626,161

(22) Filed: Feb. 19, 2015

(65) Prior Publication Data

US 2016/0242774 A1    Aug. 25, 2016

(51) Int. Cl.
*A61B 17/072*    (2006.01)

(52) U.S. Cl.
CPC .......... *A61B 17/07207* (2013.01); *A61B 2017/07271* (2013.01); *A61B 2017/07285* (2013.01)

(58) Field of Classification Search
CPC ... A61B 17/068; A61B 17/032; A61B 17/072; A61B 17/07207; A61B 2017/07271; A61B 2017/07285
USPC ...................................................... 227/180.1
See application file for complete search history.

(56) References Cited

U.S. PATENT DOCUMENTS

| | | | |
|---|---|---|---|
| 4,111,206 A * | 9/1978 | Vishnevsky | A61B 17/07207 227/176.1 |
| 4,203,444 A * | 5/1980 | Bonnell | A61B 17/32002 600/565 |
| 4,290,542 A * | 9/1981 | Fedotov | A61B 17/07207 227/155 |
| 4,868,985 A * | 9/1989 | Rehm | B26B 5/003 30/162 |
| 6,997,934 B2 * | 2/2006 | Snow | A61B 17/32075 606/159 |
| 8,070,033 B2 | 12/2011 | Milliman et al. | |
| 9,445,816 B2 * | 9/2016 | Swayze | A61B 17/1155 |
| 2004/0199182 A1 * | 10/2004 | Milliman | A61B 17/11 606/139 |
| 2005/0010241 A1 * | 1/2005 | Milliman | A61B 17/11 606/153 |
| 2008/0283576 A1 * | 11/2008 | Boyden | A61B 17/068 227/180.1 |
| 2010/0187286 A1 * | 7/2010 | Chen | A61B 17/072 227/180.1 |

(Continued)

FOREIGN PATENT DOCUMENTS

CN        101966093 A        2/2011

OTHER PUBLICATIONS

European Search Report dated Jul. 6, 2016 in corresponding EP Application No. 16156253.3-1654.

*Primary Examiner* — Hemant M Desai
*Assistant Examiner* — Valentin Neacsu

(57) ABSTRACT

In one aspect of the present disclosure a surgical stapling apparatus is disclosed including an anvil plate, a cartridge plate, and a knife assembly. The anvil and cartridge plates each include a central longitudinal slot. The longitudinal slot of the anvil plate has first and second sides each forming a toothed rack. The knife assembly includes a circular knife adapted to cut tissue is rotatably attached to an I-beam. The knife blade may have a serrated edge configured to interlock with each of the teeth of the toothed racks. The knife assembly may include at least one gear fixedly coupled to the circular knife. The at least one gear may engage the toothed rack to rotate the circular knife.

15 Claims, 11 Drawing Sheets

(56) References Cited

U.S. PATENT DOCUMENTS

| | | | |
|---|---|---|---|
| 2011/0196286 A1* | 8/2011 | Robertson | A61B 17/320068 604/22 |
| 2011/0196287 A1* | 8/2011 | Robertson | A61B 17/320068 604/22 |
| 2011/0196398 A1* | 8/2011 | Robertson | A61B 17/32002 606/169 |
| 2011/0196399 A1* | 8/2011 | Robertson | A61B 17/22004 606/169 |
| 2012/0029272 A1 | 2/2012 | Shelton, IV et al. | |
| 2014/0103092 A1 | 4/2014 | Kostrzewski et al. | |
| 2014/0166727 A1* | 6/2014 | Swayze | A61B 17/1155 227/179.1 |

* cited by examiner

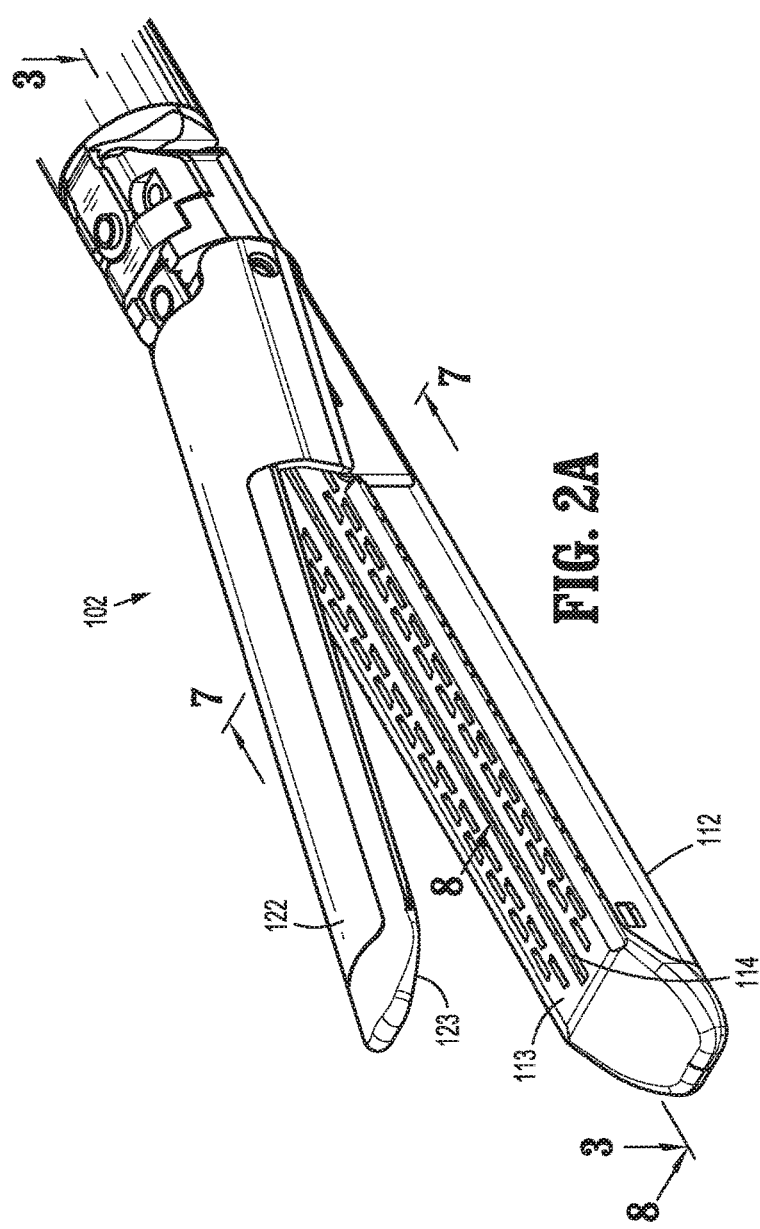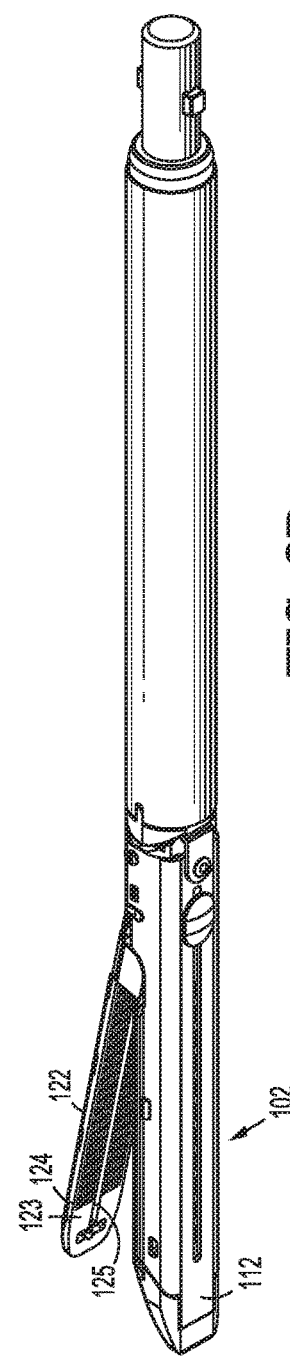

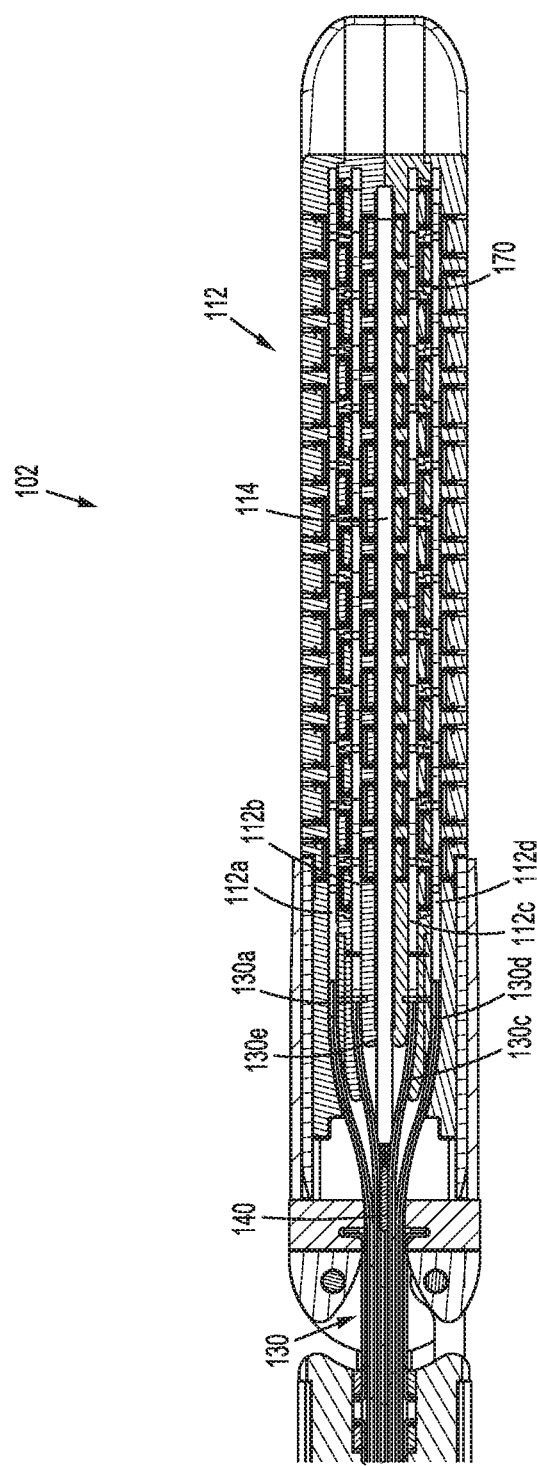

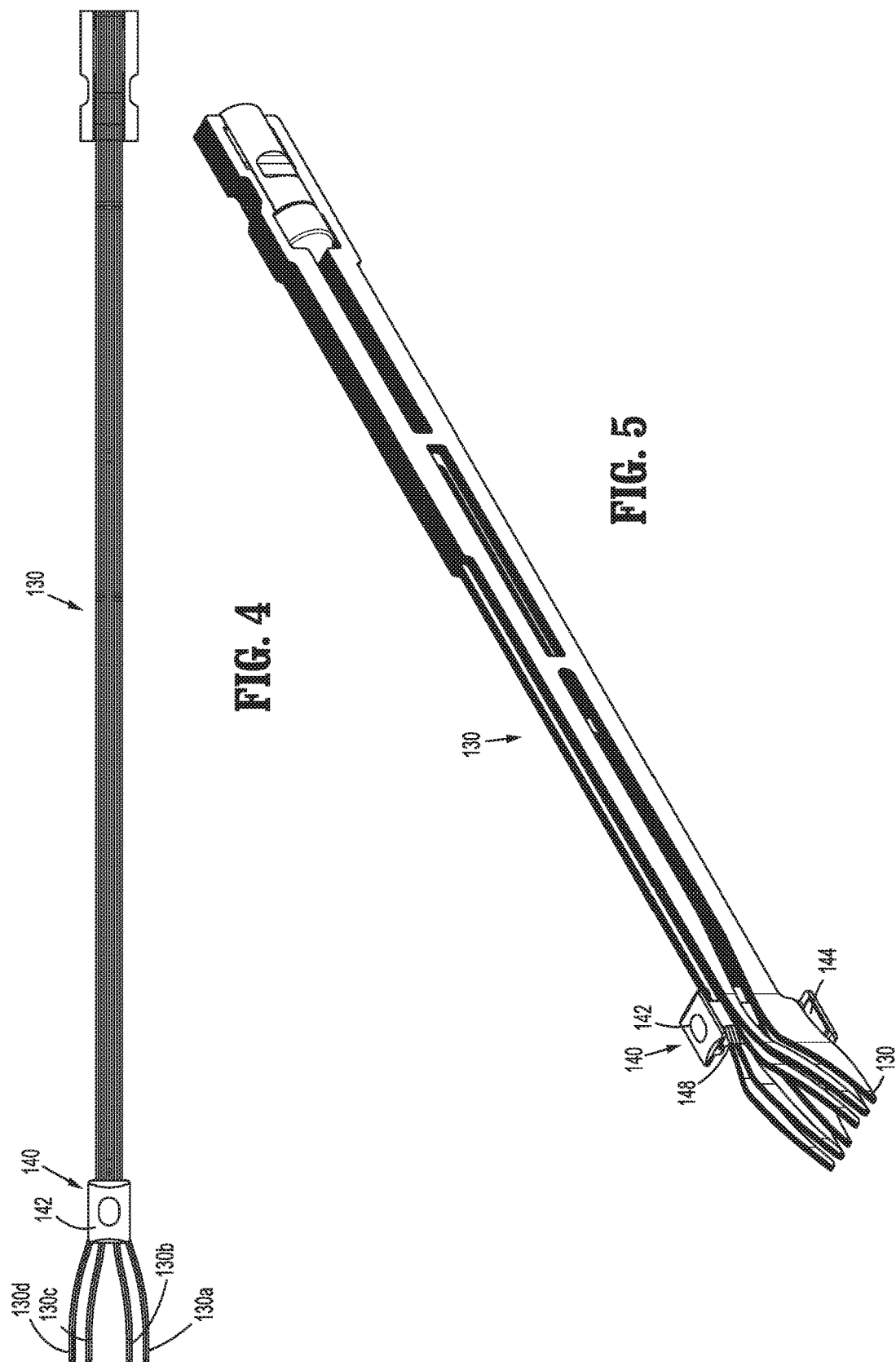

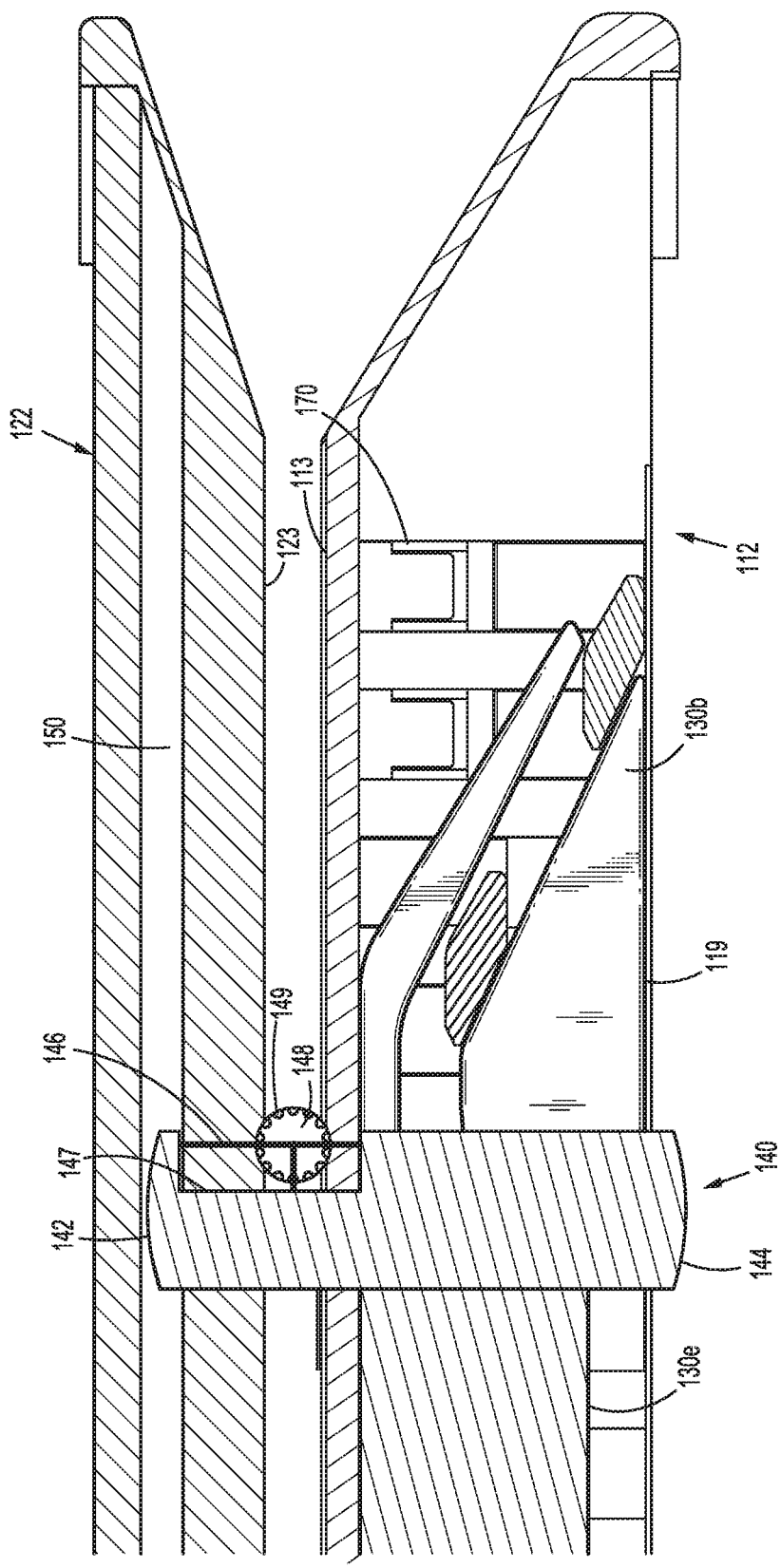

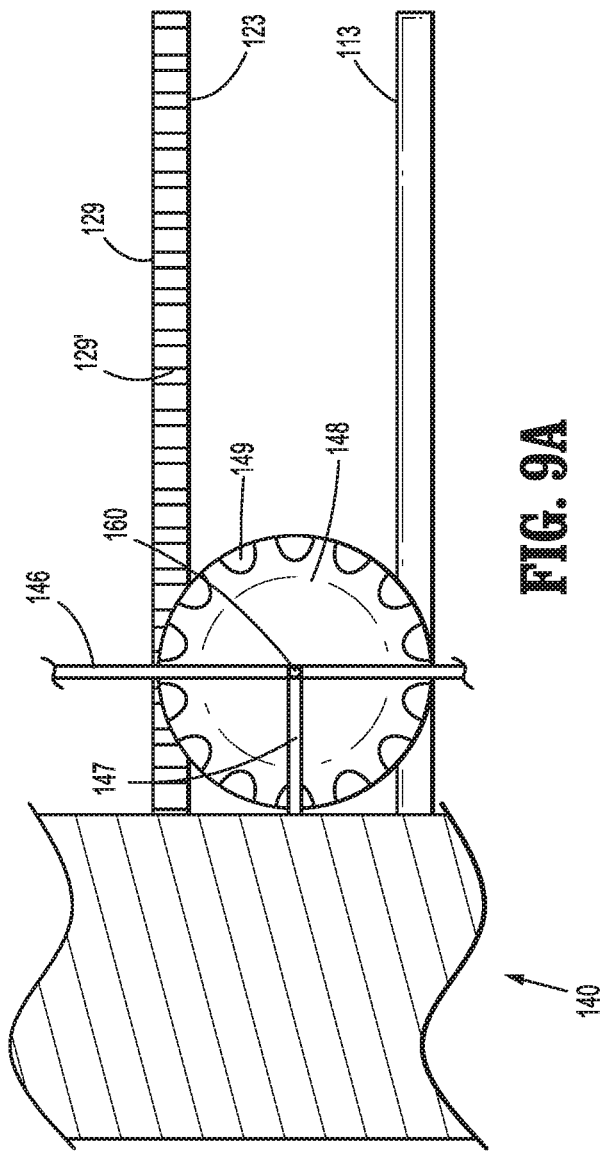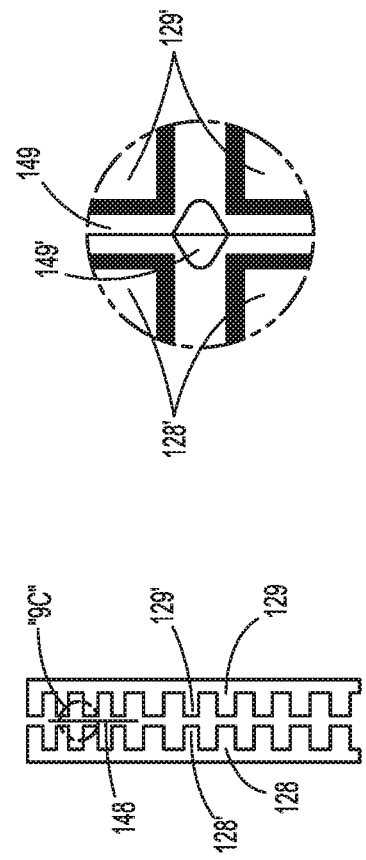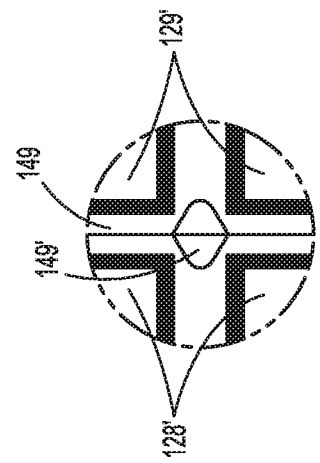

CIRCULAR KNIFE BLADE FOR LINEAR STAPLERS

BACKGROUND

Technical Field

This application relates to a surgical stapling apparatus, and more particularly, to a linear surgical stapling instrument that includes a knife.

Background of Related Art

Surgical instruments wherein tissue is first grasped or clamped between opposing jaw structure and then joined by surgical fasteners are well known in the art. In some surgical instruments a knife is provided to cut the tissue which has been joined by the fasteners. The fasteners are typically in the form of surgical staples but two part polymeric fasteners can also be utilized.

Surgical instruments for this purpose can include two elongated members which are respectively used to capture or clamp tissue. Typically, one of the members is a staple cartridge which includes a tissue contacting surface and houses a plurality of staples arranged in at least two lateral rows while the other member is an anvil which includes an anvil plate as the tissue contacting surface and defines a surface for forming the staple legs as the staples are driven from the staple cartridge. Generally, the stapling operation is effected by a cam bar, a drive sled or other similar mechanism, that travels longitudinally through the staple cartridge and acts upon staple pushers to sequentially eject the staples from the staple cartridge. A knife can travel between the staple rows to longitudinally cut and/or open the stapled tissue between the rows of staples.

In endoscopic or laparoscopic procedures, surgery is performed through a small incision or through a narrow cannula inserted through small entrance wounds in the skin. In order to address the specific needs of endoscopic and/or laparoscopic surgical procedures, endoscopic surgical stapling instruments have been developed. An example of an endoscopic surgical stapling instrument is disclosed, for example, in U.S. Pat. No. 8,070,033 to Milliman et al. and U.S. Patent App. Pub. No. 2014/0103092 to Kostrzewski et al. and the entire contents of which are incorporated herein by reference.

It would be extremely beneficial to provide a surgical instrument for use during laparoscopic and/or endoscopic surgical procedures that can be employed to improve the ability to cut tissue, reducing the force required by the operator and increasing the fatigue life of the surgical instrument.

SUMMARY

In accordance with the present disclosure, a surgical stapling apparatus for sequentially applying a plurality of fasteners to body tissue and simultaneously incising tissue is provided. The surgical stapling apparatus includes a handle assembly, an elongated body extending distally from the handle assembly and defining a longitudinal axis, and an end effector supported at the distal end of the elongated body. The end effector includes an anvil assembly, a cartridge assembly, and a drive bar. The drive bar is disposed inside the end effector and configured to move between a first position and a second position to actuate the end effector. A circular blade is rotatably attached to the drive bar. The circular blade may have a serrated edge.

In an aspect of the present disclosure, the drive bar is attached to the center of the circular blade by a connection pin.

In an aspect of the present disclosure, the anvil assembly includes an anvil plate defining a longitudinal slot having a first side and a second side.

In an aspect of the present disclosure, the cartridge assembly includes a cartridge plate defining a longitudinal slot.

In an aspect of the present disclosure, the first side of the longitudinal slot of the anvil plate defines a toothed rack. The toothed rack may be configured to engage the serrated edge of the circular blade.

In an aspect of the present disclosure, the first and second sides of the longitudinal slot of the anvil plate each define a toothed rack. In aspects, each toothed rack is configured to engage the serrated edge of the circular blade.

In an aspect of the present disclosure, moving the drive bar between the first position and the second position engages the serrated edge of the circular blade with the toothed rack of the anvil plate causing the circular blade to rotate.

In an aspect of the present disclosure, the circular blade is configured to rotate in a first direction and translate distally when the drive bar moves from the first position to the second position.

In an aspect of the present disclosure, the circular blade is configured to rotate in a second direction that is different from the first direction and translate proximally when the drive bar moves from the second to the first position.

In an aspect of the present disclosure, the circular blade is configured to rotate in a first direction such that moving the drive bar from the first position to the second position pushes tissue disposed between the anvil assembly and the cartridge assembly toward the cartridge assembly.

In an aspect of the present disclosure, the circular blade is partially disposed in the longitudinal slot of the cartridge plate.

In an aspect of the present disclosure, the knife assembly may include at least one gear fixedly coupled to the circular blade.

In an aspect of the present disclosure, the circular blade is attached to the at least one gear by a connection pin.

In an aspect of the present disclosure, the anvil plate defines a longitudinal slot. The longitudinal slot has a first side and a second side. The first side of the longitudinal slot forms a toothed rack configured to engage the at least one gear of the knife assembly.

In an aspect of the present disclosure, the anvil plate defines a longitudinal slot, the longitudinal slot having a first side and a second side, each of the first and second sides of the longitudinal slot form a toothed rack. The knife assembly may include two gears, each of the two gears being configured to engage a respective toothed rack.

In an aspect of the present disclosure, moving the drive bar assembly between the first position and the second position engages the at least one gear with the toothed rack of the anvil plate causing the circular blade to rotate.

In an aspect of the present disclosure, the circular blade is configured to rotate in a first direction and translate distally when the drive bar assembly moves from the first position to the second position.

In an aspect of the present disclosure, the circular blade is configured to rotate in a second direction that is different from the first direction and translate proximally when the drive bar assembly moves from the second to the first position.

In an aspect of the present disclosure, moving the drive bar assembly from the first position to the second position rotates the circular blade in a first direction such that tissue disposed between the anvil assembly and the cartridge assembly is pushed toward the cartridge assembly.

In an aspect of the present disclosure, moving the drive bar assembly from the first position to the second position rotates the circular blade in a first direction such that tissue disposed between the anvil assembly and the cartridge assembly is pushed toward the anvil assembly.

In another aspect of the present disclosure, an end effector comprises an anvil assembly including an anvil plate defining a longitudinal slot, and a cartridge assembly including a cartridge plate defining a longitudinal slot. The end effector further comprises a drive bar translatable through the end effector. In aspects, a distal end of the drive bar includes a vertical strut and a circular blade rotatably attached to the distal end of the drive bar. The circular blade is supported by the vertical strut of the drive bar.

In an aspect of the present disclosure, the drive bar is attached to the center of the circular blade by a connection pin.

In an aspect of the present disclosure, the longitudinal slot of the anvil plate defines at least one toothed rack.

In an aspect of the present disclosure, the circular blade has a serrated edge configured to engage the at least one toothed rack of the anvil plate.

In an aspect of the present disclosure, the circular blade is configured to rotate in a first direction and translate distally when the drive bar moves from a proximal position to a distal position.

In an aspect of the present disclosure, the circular blade is configured to rotate in a second direction and translate proximally when the drive bar moves from the distal to the proximal position.

In an aspect of the present disclosure, the circular blade is partially disposed in the longitudinal slot of the cartridge plate.

In an aspect of the present disclosure, translating the drive bar between the proximal and distal positions engages the serrated edge of the circular blade with each toothed rack of the anvil plate causing the circular blade to rotate.

In an aspect of the present disclosure, the knife assembly may include at least one gear fixedly coupled to the circular blade. The circular blade may be attached to the at least one gear by a connection pin.

In an aspect of the present disclosure, the anvil plate defines a longitudinal slot. The longitudinal slot has a first side and a second side, the first side of the longitudinal slot forming a toothed rack configured to engage the at least one gear of the knife assembly.

In an aspect of the present disclosure, the anvil plate defines a longitudinal slot. The longitudinal slot has a first side and a second side, each of the first and second sides of the longitudinal slot form a toothed rack. The knife assembly may include two gears, each of the two gears are configured to engage a respective toothed rack.

In an aspect of the present disclosure, moving the drive bar assembly between the first position and the second position engages the at least one gear with the toothed rack of the anvil plate causing the circular blade to rotate.

In an aspect of the present disclosure, the circular blade is configured to rotate in a first direction and translate distally when the drive bar assembly moves from the first position to the second position.

In an aspect of the present disclosure, the circular blade is configured to rotate in a second direction that is different from the first direction and translate proximally when the drive bar assembly moves from the second to the first position.

In an aspect of the present disclosure, moving the drive bar assembly from the first position to the second position rotates the circular blade in a first direction such that tissue disposed between the anvil assembly and the cartridge assembly is pushed toward the cartridge assembly.

In an aspect of the present disclosure, moving the drive bar assembly from the first position to the second position rotates the circular blade in a first direction such that tissue disposed between the anvil assembly and the cartridge assembly is pushed toward the anvil assembly.

In another aspect of the present disclosure, a knife assembly comprises an I-beam, a circular blade, and at least one connection member. The circular blade is rotatably attached to the distal end of the knife assembly and is supported by the at least one connection member.

In an aspect of the present disclosure, a center of the circular blade is rotatably attached to the at least one connection member by a connection pin.

In an aspect of the present disclosure, the circular blade has a serrated edge.

In an aspect of the present disclosure, the knife assembly further includes at least one gear fixedly coupled to the circular blade.

In another aspect of the present disclosure, a method of joining tissue includes a surgical stapling instrument having an end effector. The end effector has an anvil assembly including an anvil plate defining a longitudinal slot forming at least one toothed rack, a cartridge assembly, a drive bar movable through the end effector, and a circular blade rotatably attached to the drive bar. In aspects, the circular blade has a serrated edge configured to engage the at least one toothed rack of the anvil plate. In aspects, the method of joining tissue further includes approximating the end effector in an open configuration over tissue and closing the end effector in a clamping configuration such that tissue is held between the anvil assembly and the cartridge assembly. In aspects, the method of joining tissue further includes moving the drive bar from a first position to a second position, causing the serrated edge of the circular blade to engage the at least one toothed rack of the anvil plate thereby rotating the circular blade. In aspects, the method of joining tissue further includes cutting tissue with the circular blade.

In an aspect of the present disclosure, the circular blade rotates in a first direction such that tissue is pushed against the cartridge assembly.

In an aspect of the present disclosure, sliding the drive bar the first position of the second position causes the serrated edge of the circular blade to engage the at least one toothed rack of the anvil plate thereby rotating the circular blade.

In an aspect of the present disclosure, the knife assembly may include at least one gear fixedly coupled to the circular blade, the at least one gear being configured to engage the at least one toothed rack of the anvil plate.

In an aspect of the present disclosure, moving the drive bar from the first position to the second position causes the at least one gear of the knife assembly to engage the at least one toothed rack of the anvil plate thereby rotating the circular blade.

In an aspect of the present disclosure, the step of cutting tissue with the circular blade includes rotating the circular blade in a first direction such that tissue is pushed against the anvil assembly.

Any of the above aspects of the present disclosure described may be combined with any other aspect of the present disclosure without departing from the scope of the present disclosure.

BRIEF DESCRIPTION OF THE DRAWINGS

The accompanying drawings, which are incorporated in and constitute a part of this specification, illustrate embodiments of the disclosure and, together with a general description of the disclosure given above and the detailed description of the embodiments given below, serve to explain the principles of the disclosure, wherein:

FIGS. 2A and 2B are perspective views of the end effector of the surgical stapling apparatus of FIG. 1;

FIG. 3 is a top cross-sectional view of the end effector of FIG. 2A, taken along section line 3-3;

FIG. 4 is a top plan view of the drive bar assembly of the cartridge assembly of the surgical stapling apparatus of FIG. 1;

FIG. 5 is a perspective view of the drive bar assembly and knife assembly of the surgical stapling apparatus of FIG. 1;

FIG. 8 is a side cross-sectional view of the end effector of FIG. 2A, taken along section line 8-8, illustrating the knife assembly disposed in the central channels of the cartridge and anvil assemblies;

FIG. 9A is an enlargement of the knife assembly, the toothed rack of the anvil plate, and the cartridge plate of the surgical stapling apparatus of FIG. 8;

FIG. 9B is a top plan view of the toothed rack of the anvil plate and knife blade of FIG. 9A;

FIG. 9C is an enlarged view of the detail area "9C" of FIG. 9B;

DETAILED DESCRIPTION OF EMBODIMENTS

Embodiments of the presently disclosed surgical stapling apparatus will now be described in detail with reference to the drawings wherein like numerals designate identical or corresponding elements in each of the several views. As is common in the art, the term "proximal" refers to that part or component closer to the user or operator, while the term "distal" refers to that part or component farther away from the user.

Figure 1:
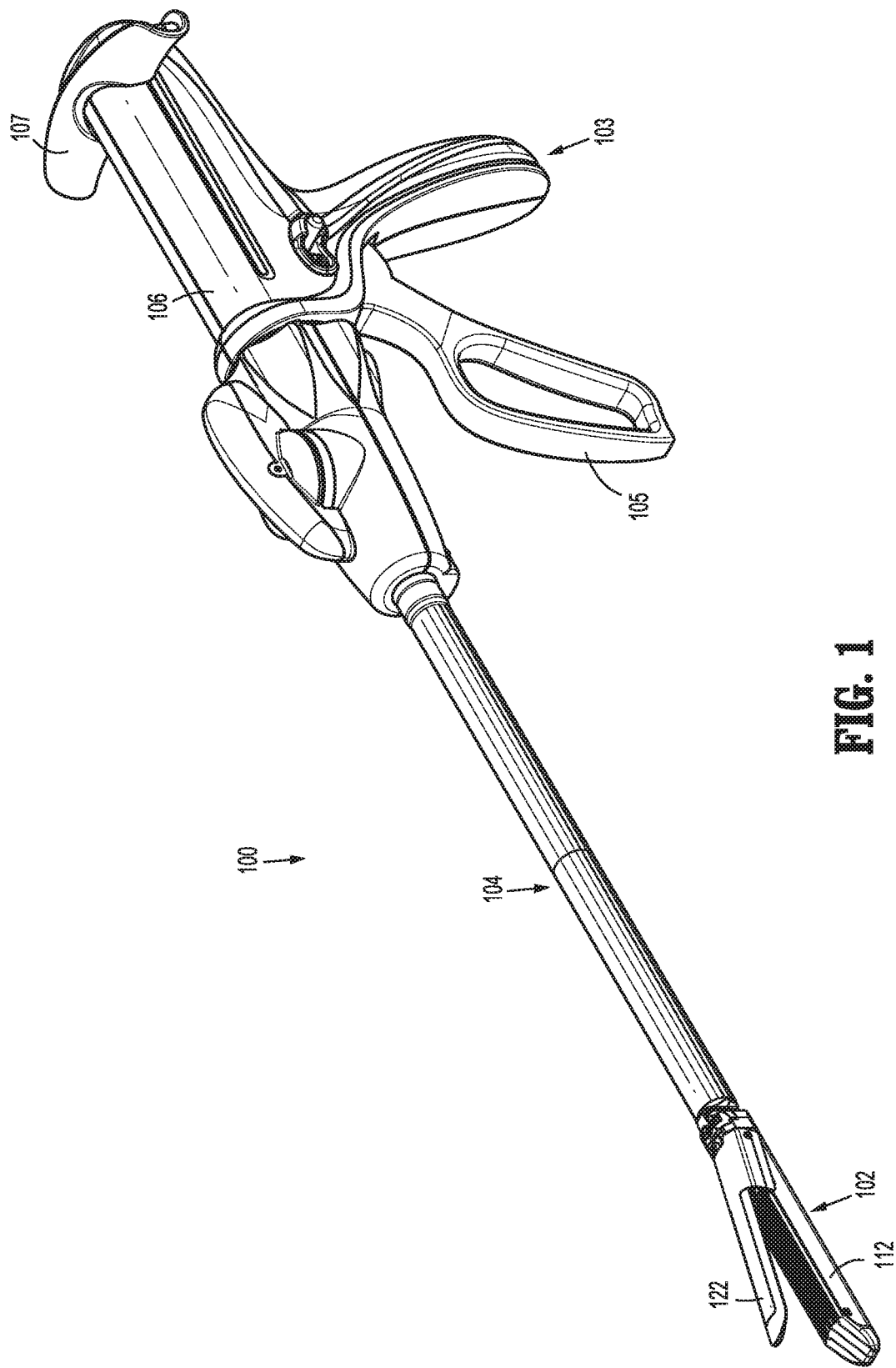
FIG. 1 is a perspective view of an exemplary surgical stapling apparatus according to the present disclosure.

FIGS. 1, 2A, and 2B illustrate one embodiment of the presently disclosed surgical stapling apparatus shown generally as 100. Briefly, surgical stapling apparatus 100 generally includes a housing assembly 103 and an elongated body 104. The elongated body 104 includes an end effector 102 having a cartridge assembly 112 housing a plurality of surgical staples and an anvil assembly 122 pivotably coupled in relation to cartridge assembly 112. A detailed description of the function of housing assembly 103, and end effector 102 are disclosed in U.S. Pat. No. 8,070,033 to Milliman et al. and U.S. Patent App. Pub. No. 2014/0103092 to Kostrzewski et al. already incorporated herein by reference.

Housing assembly 103 includes a movable handle member 105, a barrel portion 106 and a retraction member 107. Movable handle member 105 is operably coupled to end effector 102 such that upon actuation of movable handle member 105, end effector 102 is also actuated to grasp tissue, fire, and form fasteners through the grasped tissue and/or cut tissue.

A refraction member 107 is movably positioned along barrel portion 106 and operatively associated with end effector 102. Retraction member 107 is actuatable to move end effector assembly 102 between a pre-fired and fired position. During operation, as movable handle member 105 is actuated to fire the surgical stapling instrument, retraction member 107 is translated distally. Although a manually operated handle assembly is shown, it is contemplated that the instrument has a powered assembly such as one or more motors or that the end effector is a detachable component that can connect to a powered assembly, powered handle, robotic system, etc.

Figure 7:
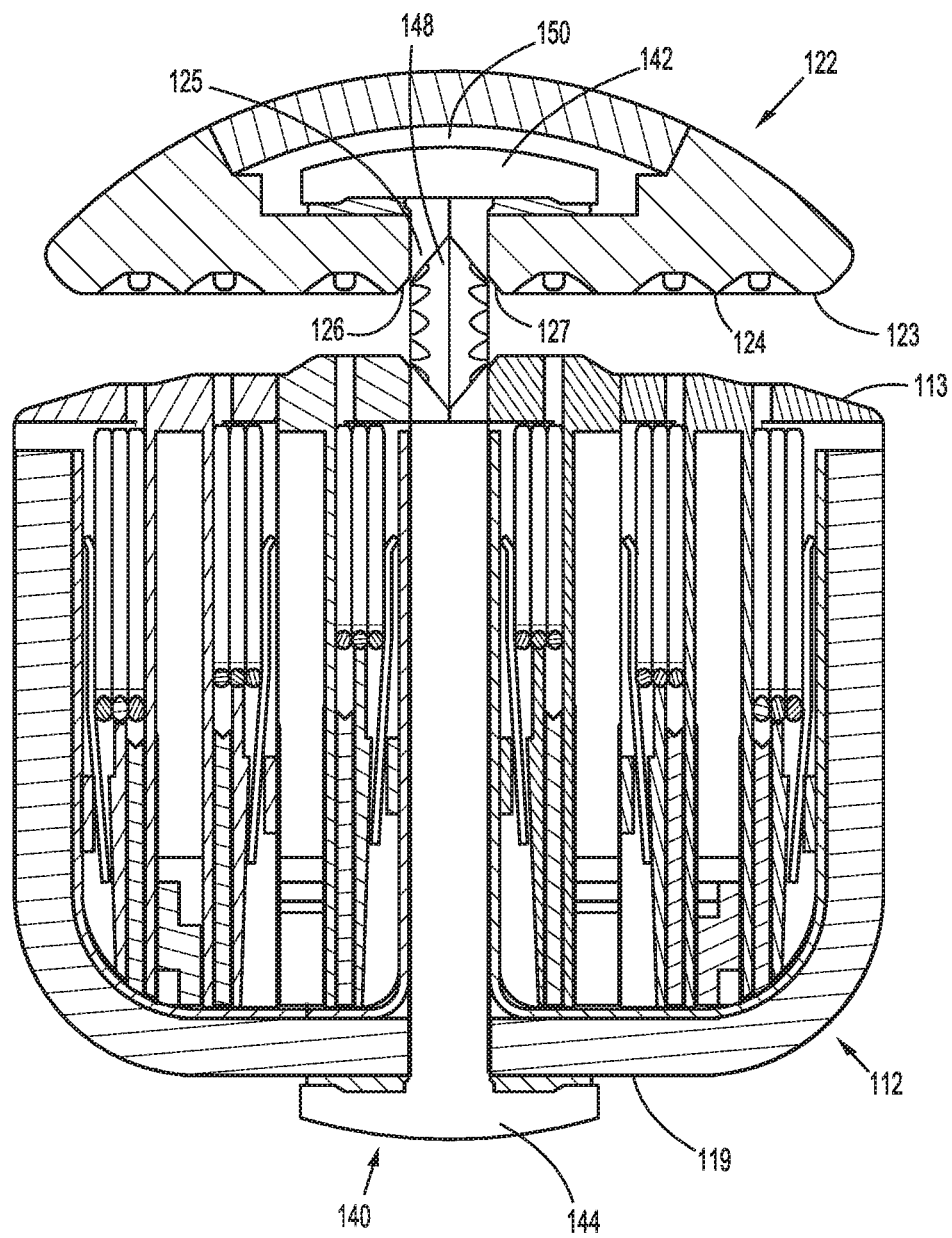
FIG. 7 is an end cross-sectional view of the end effector of FIG. 2A taken along section line 7-7, illustrating the knife assembly disposed in the central channels of the cartridge and anvil assemblies.

End effector 102 preferably includes cartridge assembly 112, anvil assembly 122, drive bar assembly 130 (FIG. 4) and knife assembly 140 (FIGS. 7 and 8). Cartridge assembly 112 includes a central longitudinal slot 114 extending at least partially therethrough to facilitate passage of the drive bar assembly 130 and knife assembly 140.

As shown in FIG. 2B, anvil assembly 122 has an anvil plate 123 defining staple forming pockets 124 and a central longitudinal slot 125 to facilitate passage of the knife assembly 140. The central longitudinal slot 125 has a first side 126 (FIG. 7) and a second side 127 (FIG. 7), where each of the first and second sides 126, 127 defines a toothed rack 128, 129 (FIG. 9B). However, in another embodiment, only one of the first and second sides 126, 127 may form the toothed rack. In operation, tissue is grasped between the cartridge plate 113 and anvil plate 123 of the cartridge and anvil assemblies 112, 122.

Referring to FIG. 3, a drive bar assembly 130 is disposed at least partially within proximal end of end effector 102 and in operative communication with housing assembly 103. It is configured to housing assembly 103 such that actuation of handle assembly 105 and retraction member 107 cause drive bar assembly 130 and knife assembly 140 to translate distally and proximally through end effector 102, as will be described below in more detail.

Drive bar assembly 130 includes a plurality of drive bars 130a-130d coupled to a central drive member 130e. As discussed above, a central longitudinal slot 114 extends along the length of cartridge assembly 112 to facilitate passage of central drive member 130e therethrough.

As end effector 102 is actuated, drive bars 130a-e of drive bar assembly 130 translate through the longitudinal slots 112a-d, 114 of the cartridge assembly 112. As the drive bars 130a-d translate distally, staples 170 are ejected from the cartridge assembly 112, through tissue disposed between the cartridge and anvil plates 113, 123, and against staple forming pockets 124 of anvil assembly 122 for staple forming.

Figure 6:
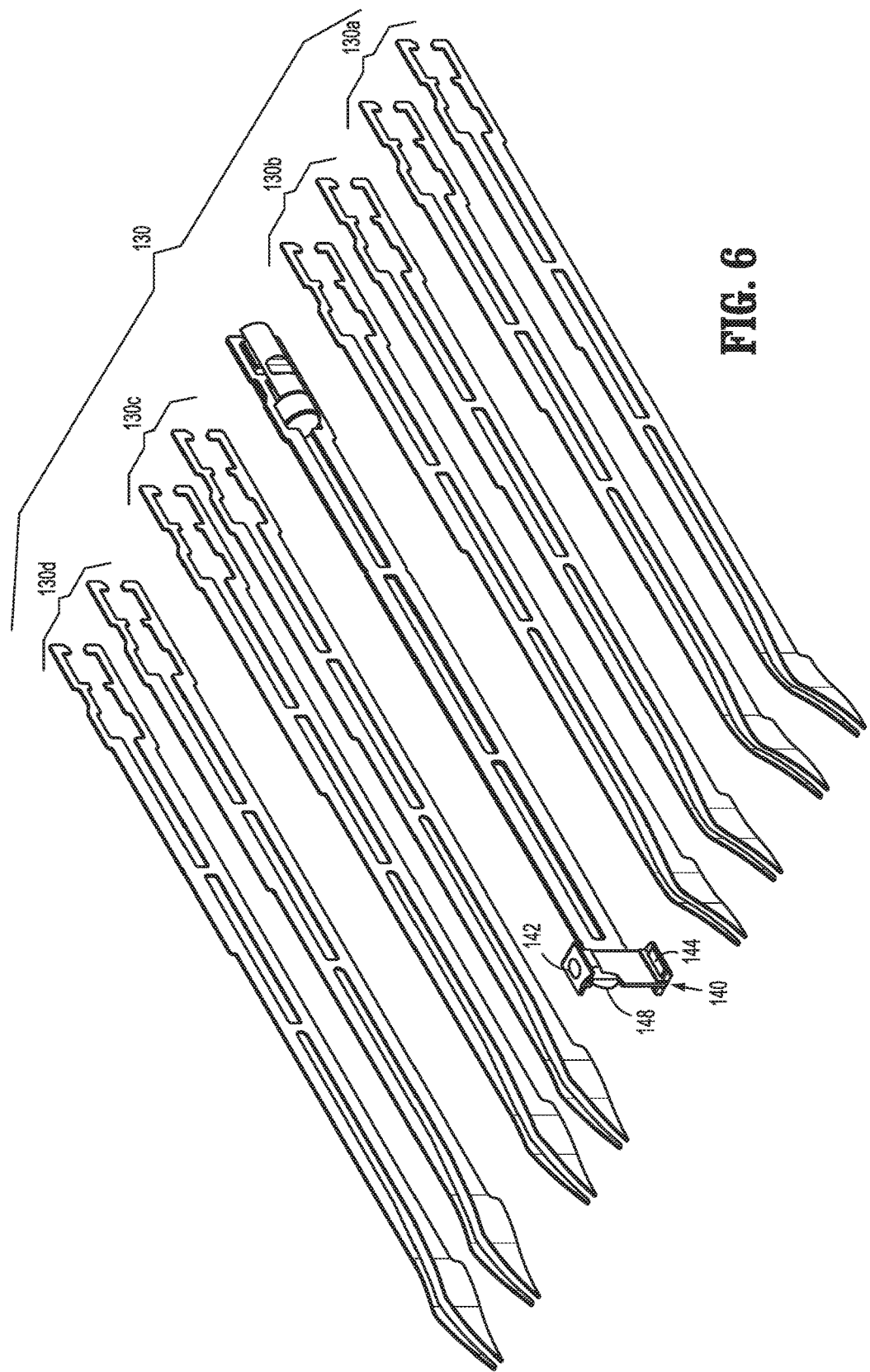
FIG. 6 is an exploded view of the drive bar assembly and knife assembly of FIG. 5.

Now referring to FIGS. 4, 5, and 6, drive bars 130*a-d* and central drive member 130*e* are initially disposed adjacent to one another within cartridge assembly 112 of end effector 102. Drive bars 130*a-d* are resilient or flexible such that they may spread out to translate through longitudinal slots 112*a-d*. It is contemplated, for example, that each longitudinal slot 112*a-d* may accommodate passage of a single drive bar or may accommodate passage of multiple drive bars.

Central drive member 130*e* is elongate in shape and includes knife assembly 140 attached to the distal end thereof. Knife assembly 140 defines a substantially I-shaped cross section having a top flange 142, a bottom flange 144, connection members 146, 147 (FIG. 8) and a knife blade 148. The knife assembly 140 is positioned on the central drive member 130*e* such that the drive bars 130*a-d* cause stapling of tissue before the knife assembly 140 cuts tissue.

With reference now to FIGS. 7 and 8, top flange 142 of knife assembly 140 is configured to translate through an interior slot 150 of anvil assembly 122 while bottom flange 144 is configured to translate longitudinally along an underside 119 of cartridge assembly 112.

Knife blade 148 of knife assembly 140 includes a serrated edge 149 and is attached to connection members 146, 147 at its center via a connection pin 160. Connection pin 160 enables knife blade 148 to rotate relative to the cartridge and anvil plates 113, 123. Central longitudinal slot 125 of the anvil plate 123 forms first and second sides 126, 127, where first and second sides 126, 127 define toothed racks 128, 129.

Now referring to FIGS. 9A-9C, toothed racks 128, 129 of anvil plate 123 are configured to interlock with serrated edge 149 of knife blade 148. As previously mentioned, knife blade 148 is rotatably attached to knife assembly 140. As shown in FIG. 9A, applying a linear force to knife assembly 140 causes rotational movement of knife blade 148. As shown in FIGS. 9B and 9C, each of the toothed racks 128, 129 form a plurality of teeth 128', 129'. Serrated edge 149 of knife blade 148 defines a surface having gear-like protuberances 149'. Each toothed rack 128, 129 are dimensioned such that each of the plurality of teeth 128', 129' are configured to engage the gear-like protuberances 149' of serrated edge 149. As shown in FIGS. 9A and 9C, since knife blade 148 is rotatably attached to knife assembly 140, when a linear force is applied to knife assembly 140, gear-like protuberances 149' of serrated edge 149 contacts the plurality of teeth 128', 129' and then gear-like protuberances 149' are, essentially, urged to rotate in a first direction thereby rotating knife blade 148.

Referring back to FIGS. 7 and 8, in operation, as knife assembly 140 translates through cartridge and anvil assemblies 112, 122, serrated edge 149 of knife blade 148 interlocks with each of the teeth 128', 129' of toothed racks 128, 129. The gear-like configuration of serrated edge 149 and toothed racks 128, 129 causes the knife blade 148 to rotate in a first direction when an operator translates retraction member 107 to move drive bar assembly 130 from a pre-fired to a fired position. Knife blade 148 severs the portion of tissue that is disposed between the cartridge and anvil assemblies 112, 122 as it translates from a proximal, pre-fired position to a distal, fired position.

When knife assembly 140 translates from the distal position to the proximal position, serrated edge 149 interlocks with toothed racks 128, 129 such that knife blade 148 rotates in a second direction that is different than the first.

With reference now to FIGS. 10-12B, an alternate embodiment of a knife assembly 240 is shown. Knife blade 248 of knife assembly 240 is attached to connection members 246, 247 at its center via a connection pin 260. Knife blade 248 of knife assembly 240 may have any type of appropriate edge, including a straight edge or a serrated edge.

Figure 10:
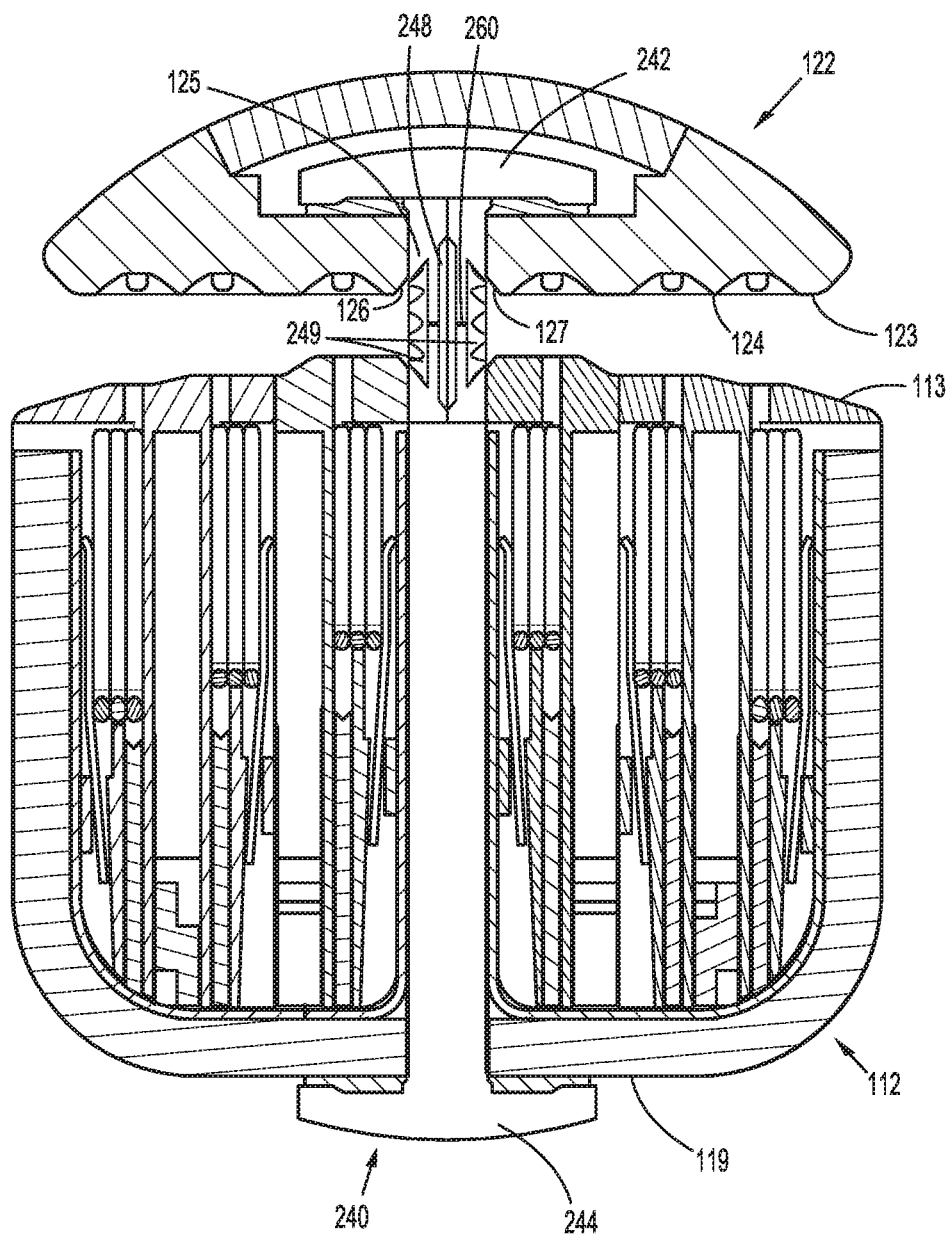
FIG. 10 is an end cross-sectional view of the end effector of FIG. 2A taken along section line 7-7, illustrating an alternative embodiment of a knife assembly disposed in the central channels of the cartridge and anvil assemblies.
Figure 11:
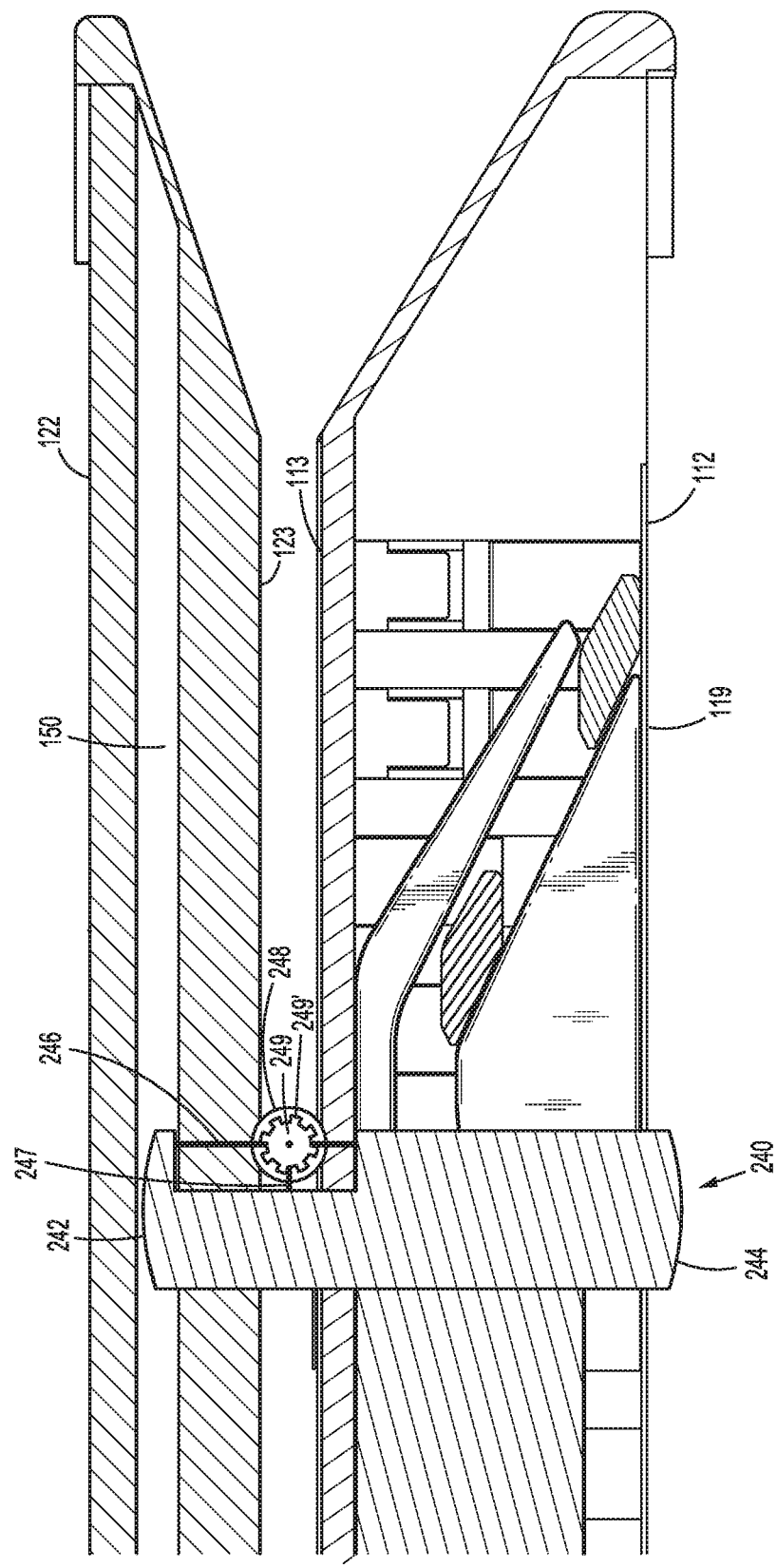
FIG. 11 is a side cross-sectional view of the end effector of FIG. 2A, taken along section line 8-8, illustrating the knife assembly of FIG. 10 disposed in the central channels of the cartridge and anvil assemblies.

Knife assembly 240 further includes gears 249 extending from and coaxial with knife blade 248. Although knife assembly 240, as shown in FIGS. 10-12, includes two gears 249, it is contemplated that a single gear 249 may be used. Each gear 249 includes a set of teeth 249'. Gears 249 are shown as bevel gears, however any other suitable type of gear may be used.

Gears 249 are coupled to knife blade 248 via a connection pin 260. Gears 249 and knife blade 248 are rigidly coupled together such that rotation of gears 249 cause knife blade 248 to rotate. Connection pin 260 is pivotally attached to connection members 246, 247. The pivotable connection between connection pin 260 and connection members 246, 247 allow gears 249 and knife blade 248 to rotate relative to the cartridge and anvil plates 113, 123. Since gears 249 and knife blade 248 are rigidly coupled together, they rotate in the same direction when translating between the proximal, pre-fired position and the distal, fired position.

Figure 12A:
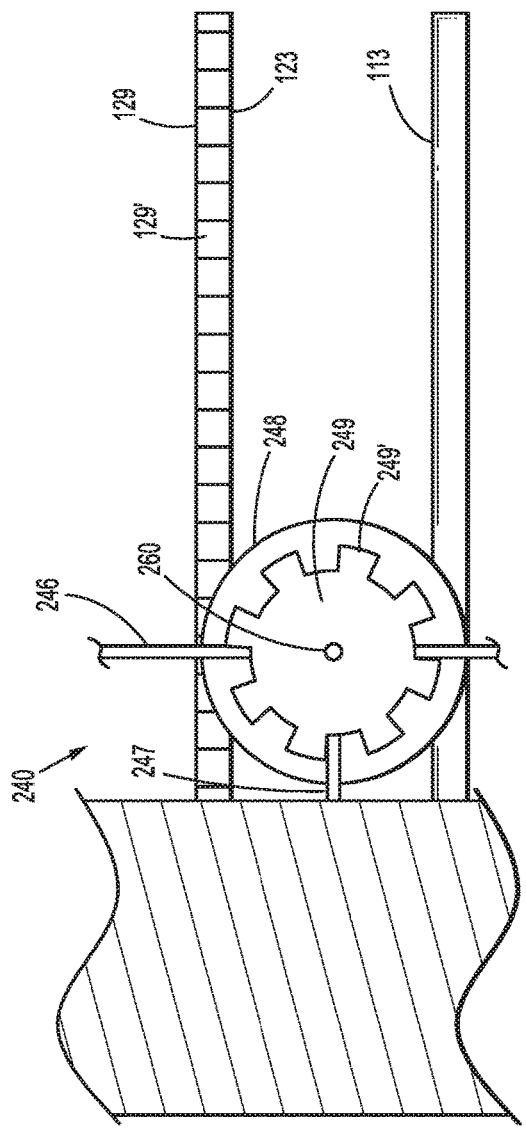
FIG. 12A is an enlargement of the knife assembly, the toothed rack of the anvil plate, and the cartridge plate of the surgical stapling apparatus of FIG. 11.
Figure 12B:
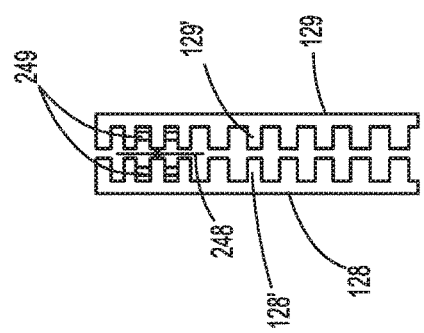
FIG. 12B is a top plan view of the toothed rack of the anvil plate and knife blade of FIG. 12A.

As shown in FIGS. 12A and 12B, each of the toothed racks 128, 129 forms a plurality of teeth 128', 129'. The configuration of toothed racks 128, 129 in FIG. 12B is similar the configuration of toothed racks 128, 129 in FIG. 9B. Each toothed rack 128, 129 is dimensioned such that each of the plurality of teeth 128', 129' is configured to interlock with gear teeth 249' of each gear 249. Since gears 249 and knife blade 248 are rotatably attached to knife assembly 240 via connection members 246, 247, when a linear force is applied to knife assembly 240, gear teeth 249' of gears 249 contact the plurality of teeth 128', 129' of the toothed racks 128, 129.

Referring back to FIGS. 10 and 11, in operation, when an operator translates retraction member 107 to move drive bar assembly 130 from a pre-fired to a fired position, knife assembly 240 translates through end effector 102. As knife assembly 240 translates, gear teeth 249' are urged by the plurality of teeth 128', 129' to rotate in a first direction thereby rotating knife blade 248 in the first direction. Rotating knife blade 248 severs the portion of tissue that is disposed between the cartridge and anvil assemblies 112, 122 as it translates from the proximal, pre-fired position to the distal, fired position.

When knife assembly 240 translates from the distal position to the proximal position, gear teeth 249' of gears 249 engages the plurality of teeth 128', 129' of toothed racks 128, 129 such that gears 249 and knife blade 248 rotate in a second direction that is different than the first direction.

In FIGS. 10-12B toothed racks 128, 129 are located on anvil plate 112. When toothed racks 128, 129 are located on anvil plate 112, knife blade 248 rotates towards cartridge plate 113 when moving from the proximal, pre-fired position to the distal, fired position. Alternatively, toothed racks 128, 129 may be located on the cartridge plate. When toothed racks 128, 129 are located on cartridge plate 113, knife blade 248 rotates towards anvil plate 112 when moving from the proximal, pre-fired position to the distal, fired position.

It is contemplated that individual features of the above-described embodiments may be combined without departing from the scope of the present disclosure.

In any of the embodiments disclosed herein, a toothed rack can be on either the cartridge assembly or anvil side; the toothed rack is in the elongated slot on either the cartridge or anvil. The location of the toothed rack would ultimately dictate the directional rotation of the knife. The cutting edge of the knife can rotate towards the cartridge, and the toothed rack is on the cartridge side, in certain embodiments.

Although the illustrative embodiments of the present disclosure have been described herein with reference to the accompanying drawings, the above description, disclosure, and figures should not be construed as limiting, but merely as exemplifications of particular embodiments. For example, it is contemplated that a rotatable knife blade as described above could be included in a surgical stapling instrument that includes an actuation sled rather than cam/drive bars, or could be included in a surgical stapling instrument that utilizes alternative means other than an I-beam to approximate the staple cartridge jaw and anvil jaw with one another. It is to be understood, therefore, that the disclosure is not limited to the precise embodiments described herein, and that various other changes and modifications may be effected by one skilled in the art without departing from the scope or spirit of the present disclosure.

What is claimed is:

1. A surgical apparatus, comprising:
   a handle assembly;
   an elongated body extending distally from the handle assembly and defining a longitudinal axis;
   an end effector supported at a distal end of the elongated body, the end effector including an anvil assembly, a cartridge assembly, and a drive bar assembly, the anvil assembly including an anvil plate defining a longitudinal slot having a first side and a second side, the drive bar assembly disposed inside the end effector and configured to move between a first position and a second position to actuate the end effector; and
   a circular blade rotatably attached to a knife assembly, the circular blade having a serrated edge, wherein the first side of the longitudinal slot of the anvil plate defines a toothed rack configured to engage the serrated edge of the circular blade.

2. The surgical apparatus of claim 1, wherein the circular blade is attached at its center by a connection pin.

3. The surgical apparatus of claim 1, wherein the cartridge assembly includes a cartridge plate defining a longitudinal slot.

4. The surgical apparatus of claim 3, wherein the circular blade is partially disposed in the longitudinal slot of the cartridge plate.

5. The surgical apparatus of claim 1, wherein the first and second sides of the longitudinal slot of the anvil plate each define a toothed rack, wherein each toothed rack is configured to engage the serrated edge of the circular blade.

6. The surgical apparatus of claim 5, wherein axial displacement of the drive bar assembly between the first position and the second position engages the serrated edge of the circular blade with each toothed rack of the anvil plate causing the circular blade to rotate.

7. The surgical apparatus of claim 6, wherein the circular blade is configured to rotate in a first direction and move distally when the drive bar assembly is transitioned from the first position to the second position.

8. The surgical apparatus of claim 7, wherein the circular blade is configured to rotate in a second direction that is different from the first direction and move proximally when the drive bar assembly transitions from the second position to the first position.

9. The surgical apparatus of claim 1, wherein the circular blade is configured to rotate in a first direction such that axial displacement of the drive bar assembly from the first position to the second position pushes tissue disposed between the anvil assembly and the cartridge assembly toward the cartridge assembly.

10. A surgical apparatus comprising:
    an elongated body defining a longitudinal axis;
    an end effector supported at a distal end of the elongated body, the end effector including an anvil assembly, a cartridge assembly, and a drive bar assembly, the anvil assembly including an anvil plate defining a longitudinal slot having a first side and a second side, the first and second sides of the longitudinal slot of the anvil plate each defining a toothed rack, the drive bar assembly disposed inside the end effector and configured to move between a first position and a second position to actuate the end effector; and
    a circular blade rotatably attached to a knife assembly, the circular blade having a serrated edge, wherein each toothed rack is configured to engage the serrated edge of the circular blade.

11. The surgical apparatus of claim 10, wherein axial displacement of the drive bar assembly between the first position and the second position causes engagement of the serrated edge of the circular blade with each toothed rack of the anvil plate, which, in turn, causes the circular blade to rotate.

12. The surgical apparatus of claim 10, wherein the circular blade is configured to rotate in a first direction and move distally when the drive bar assembly is transitioned from the first position to the second position.

13. The surgical apparatus of claim 12, wherein the circular blade is configured to rotate in a second direction that is different from the first direction and move proximally when the drive bar assembly transitions from the second position to the first position.

14. The surgical apparatus of claim 10, wherein the cartridge assembly includes a cartridge plate defining a longitudinal slot.

15. The surgical apparatus of claim 14, wherein the circular blade is partially disposed in the longitudinal slot of the cartridge plate.

* * * * *